(12) United States Patent
Agnihotram et al.

(10) Patent No.: US 9,933,353 B2
(45) Date of Patent: Apr. 3, 2018

(54) METHOD FOR ASSESSING CORRODED PIPELINE DEFECT GROWTH FROM PARTIAL INSPECTION DATA AND DEVICES THEREOF

(71) Applicant: Infosys Limited, Bangalore (IN)

(72) Inventors: Gopichand Agnihotram, Guntur (IN); Hari Manassery Koduvely, Bangalore (IN)

(73) Assignee: Infosys Limited, Bangalore (IN)

( * ) Notice: Subject to any disclaimer, the term of this patent is extended or adjusted under 35 U.S.C. 154(b) by 487 days.

(21) Appl. No.: 14/612,651

(22) Filed: Feb. 3, 2015

(65) Prior Publication Data

US 2015/0226660 A1  Aug. 13, 2015

(30) Foreign Application Priority Data

Feb. 13, 2014  (IN) .............................. 679/CHE/2014

(51) Int. Cl.
*G01B 3/52*     (2006.01)
*G01N 17/00*    (2006.01)
*G06Q 10/00*    (2012.01)
*G06F 11/30*    (2006.01)

(52) U.S. Cl.
CPC ............. *G01N 17/00* (2013.01); *G06Q 10/00* (2013.01)

(58) Field of Classification Search
CPC .................................................... G01N 17/00
See application file for complete search history.

(56) References Cited

U.S. PATENT DOCUMENTS

| | | | |
|---|---|---|---|
| 6,195,624 B1* | 2/2001 | Woodman | G06F 17/5009 702/34 |
| 7,672,793 B2 | 3/2010 | Beard | |
| 7,941,282 B2 | 5/2011 | Ziegel et al. | |
| 8,109,150 B2 | 2/2012 | Sato et al. | |
| 2006/0206295 A1 | 9/2006 | Tryon, III | |
| 2008/0289423 A1* | 11/2008 | Gordon | G01N 29/069 73/602 |

* cited by examiner

*Primary Examiner* — Phuong Huynh
(74) *Attorney, Agent, or Firm* — LeClairRyan, a Professional Corporation

(57) ABSTRACT

The technique relates to a system and method for assessing corroded pipeline defect growth rate from partial defect growth rate information. The method involves obtaining a plurality of observed defect growth rates from the inspection data collected at different time intervals then determining at least one unobserved defect growth rate on the basis of distribution pattern of the plurality of observed defect growth rates thereafter simulating condition of at least one hyper parameter on the inspection data based on prior information of the at least one hyper parameter then simulating the plurality of observed defect growth rates and the at least one unobserved defect growth rate based on the simulated hyper parameters and finally obtaining defect growth rate point estimate from the simulated growth rate data. The method also involves determining a probability of failure of a defect from the defect growth rate point estimates.

12 Claims, 3 Drawing Sheets

METHOD FOR ASSESSING CORRODED PIPELINE DEFECT GROWTH FROM PARTIAL INSPECTION DATA AND DEVICES THEREOF

This application claims the benefit of Indian Patent Application Serial No. 679/CHE/2014 filed Feb. 13, 2014, which is hereby incorporated by reference in its entirety.

FIELD

The present invention relates generally to assessing corroded pipeline defect growth rate, and in particular, to a system and method for assessing corroded pipeline defect growth from partial inspection data.

BACKGROUND

The pipelines defects are usually defects in the pipeline such as corrosion caused by temperature, stress, and inspection uncertainties etc. which may lead to uncertainties in pipelines or hamper pipeline functions. The existing technologies involve various methods to identify the defect growth rate in pipelines. The pipelines are inspected periodically for defects usually by two methods in-line and external inspection methods. In-line for example, by using Pipeline Inspection Gauges is expensive and carried out less frequently. External inspection is done more frequently, but only on critical defects, therefore practically there would be incomplete inspection data considering all the defects. The existing method involves identifying the defects or probability of failure by analyzing the inspection data taken periodically at different time intervals though there are high probabilities that data may be unobserved or missing during inspection in such cases probability of occurrence of defect cannot be analyzed. The existing technology does not provide probability of failure if inspection data is missing or unobserved.

In view of foregoing discussion, there is a need of system and method for assessing corroded pipeline defect growth from partial inspection data.

SUMMARY

The present invention overcomes the limitation mentioned above by providing a system and method for assessing corroded pipeline defect growth from partial inspection data using Hierarchical Bayesian methods.

According to the present embodiment, a method for assessing corroded pipeline defect growth rate from partial inspection data is disclosed. The method involves obtaining a plurality of observed defect growth rates from the inspection data collected at different time intervals then determining at least one unobserved defect growth rate on the basis of distribution pattern of the plurality of observed defect growth rates thereafter simulating condition of at least one hyper parameter on the inspection data based on prior information of the at least one hyper parameter then simulating the plurality of observed defect growth rates and the at least one unobserved defect growth rate based on the simulated hyper parameters and finally obtaining defect growth rate point estimate from the simulated growth rate data.

In an additional embodiment, a system for assessing corroded pipeline defect growth rate from partial inspection data is disclosed. The system includes an observed defect growth rate obtaining component, an unobserved growth rate determination component, a hyper parameter simulation component, a growth rate simulation component and a defect growth rate point estimate component. The observed defect growth rate obtaining component is configured to obtain a plurality of observed defect growth rates from the inspection data collected at different time intervals. The unobserved growth rate determination component is configured to determine at least one unobserved defect growth rate on the basis of distribution pattern of the plurality of observed defect growth rates. The hyper parameter simulation component configured to simulate, condition of at least one hyper parameter on the inspection data based on prior information of the at least one hyper parameter. The growth rate simulation component configured to simulate the plurality of observed defect growth rates and the at least one unobserved defect growth rate based on the simulated hyper parameters. The defect growth rate point estimate component configured to obtain defect growth rate point estimate from the simulated growth rate data.

In another embodiment, a non-transitory computer readable medium for assessing corroded pipeline defect growth rate from partial inspection data is disclosed. This involves a non-transitory computer readable medium having stored thereon instructions for obtaining a plurality of observed defect growth rates from the inspection data collected at different time intervals then determining at least one unobserved defect growth rate on the basis of distribution pattern of the plurality of observed defect growth rates thereafter simulating condition of at least one hyper parameter on the inspection data based on prior information of the at least one hyper parameter then simulating the plurality of observed defect growth rates and the at least one unobserved defect growth rate based on the simulated hyper parameters and finally obtaining defect growth rate point estimate from the simulated growth rate data.

BRIEF DESCRIPTION OF THE DRAWINGS

Various embodiments of the invention will, hereinafter, be described in conjunction with the appended drawings provided to illustrate, and not to limit the invention, wherein like designations denote like elements, and in which.

DETAILED DESCRIPTION

The foregoing has broadly outlined the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

Figure 1:
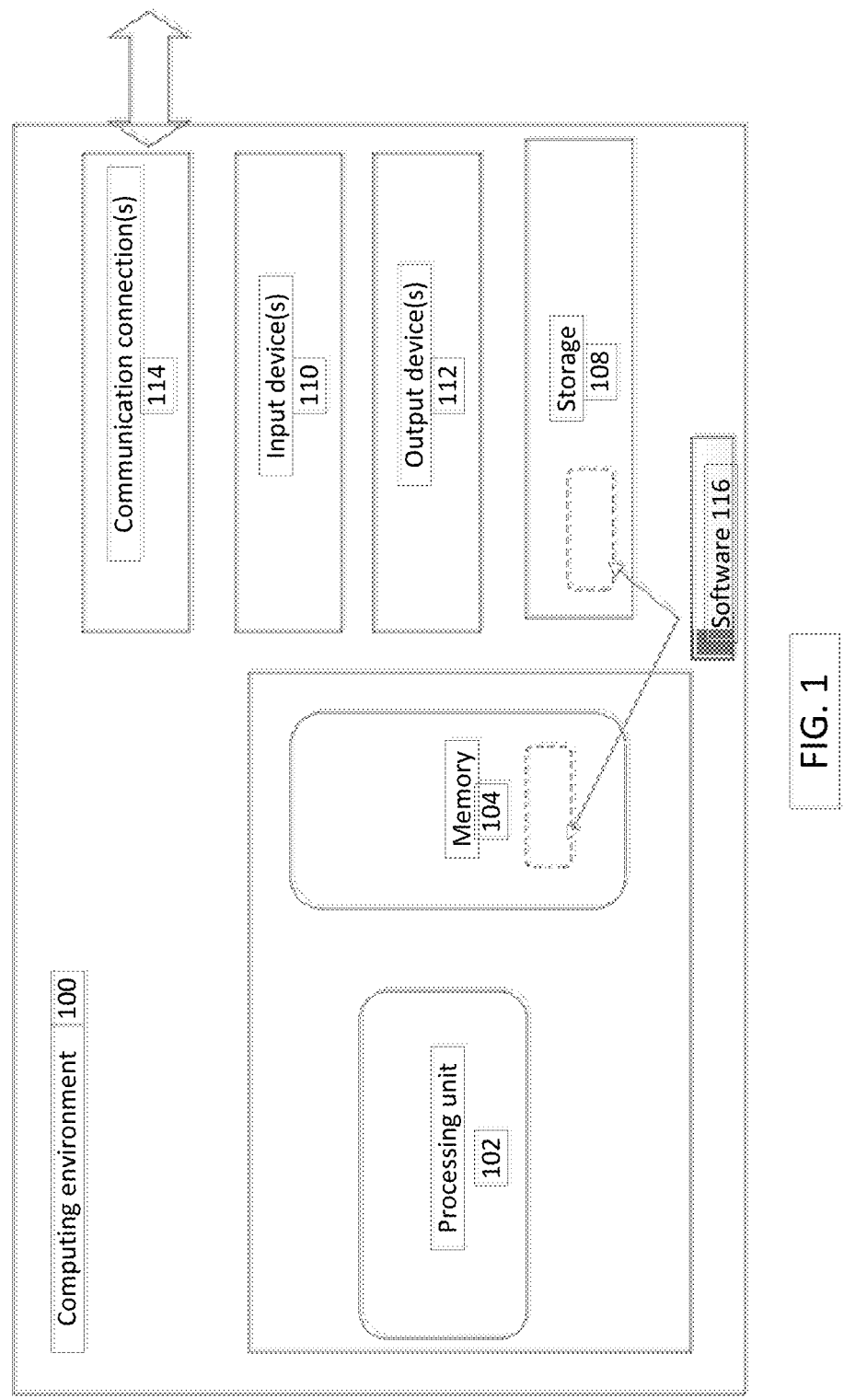
FIG. 1 is a computer architecture diagram illustrating a computing system capable of implementing the embodiments presented herein.

FIG. 1 illustrates a generalized example of a suitable computing environment 100 in which all embodiments, techniques, and technologies of this invention may be implemented. The computing environment 100 is not intended to suggest any limitation as to scope of use or functionality of the technology, as the technology may be implemented in diverse general-purpose or special-purpose computing environments. For example, the disclosed technology may be implemented using a computing device (e.g., a server, desktop, laptop, hand-held device, mobile device, PDA, etc.) comprising a processing unit, memory, and storage storing computer-executable instructions implementing the service level management technologies described herein. The disclosed technology may also be implemented with other computer system configurations, including hand held devices, multiprocessor systems, microprocessor-based or programmable consumer electronics, network PCs, minicomputers, mainframe computers, a collection of client/server systems, and the like.

With reference to FIG. 1, the computing environment 100 includes at least one central processing unit 102 and memory 104. The central processing unit 102 executes computer-executable instructions. In a multi-processing system, multiple processing units execute computer-executable instructions to increase processing power and as such, multiple processors can be running simultaneously. The memory 104 may be volatile memory (e.g., registers, cache, RAM), non-volatile memory (e.g., ROM, EEPROM, flash memory, etc.), or some combination of the two. The memory 104 stores software 116 that can implement the technologies described herein. A computing environment may have additional features. For example, the computing environment 100 includes storage 108, one or more input devices 110, one or more output devices 112, and one or more communication connections 114. An interconnection mechanism (not shown) such as a bus, a controller, or a network, interconnects the components of the computing environment 100. Typically, operating system software (not shown) provides an operating environment for other software executing in the computing environment 100, and coordinates activities of the components of the computing environment 100.

Figure 2:
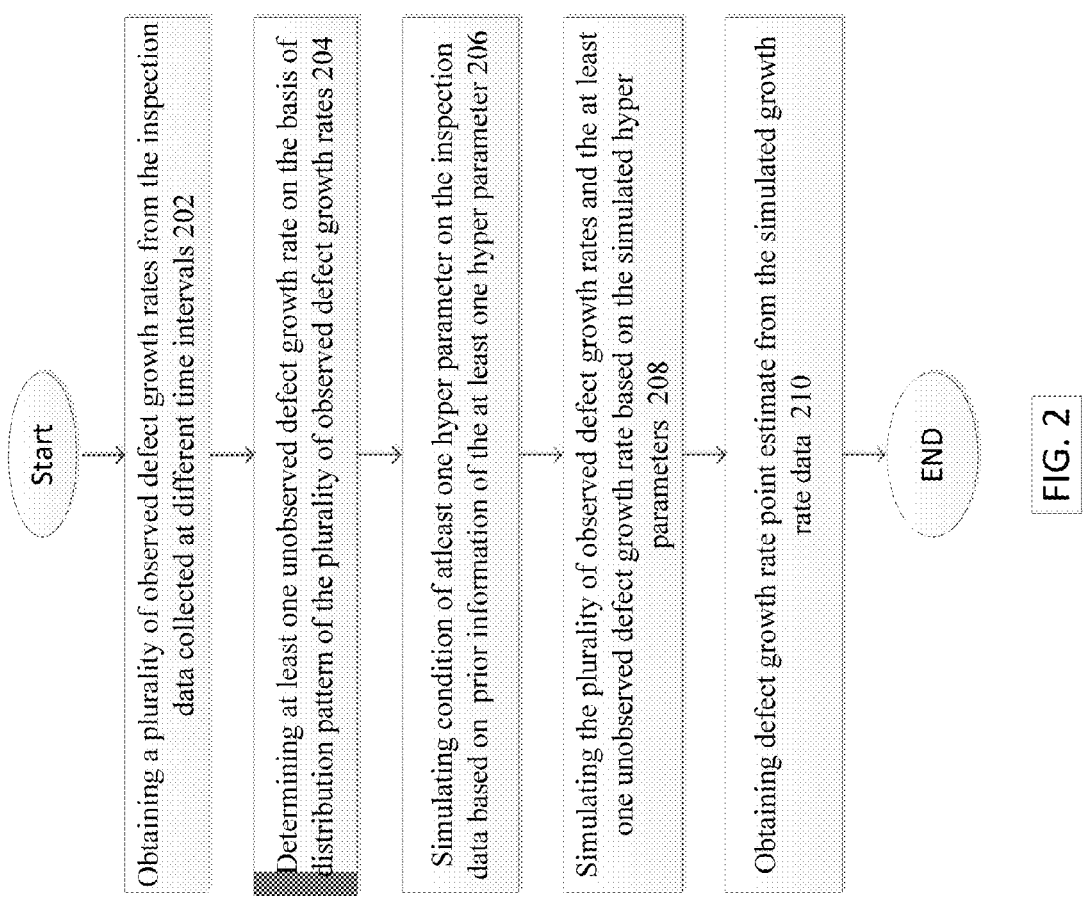
FIG. 2 is a flowchart, illustrating a method for assessing corroded pipeline defect growth rate from partial inspection data, in accordance with an embodiment of the present technique.

FIG. 2 is a flowchart, illustrating a method for assessing corroded pipeline defect growth rate from partial inspection data, in accordance with an embodiment of the present technique. A plurality of observed defect growth rates is obtained from the inspection data collected at different time intervals 202 then at least one unobserved defect growth rate is determined on the basis of distribution pattern of the plurality of observed defect growth rates 204 thereafter at least one hyper parameter is simulated on the inspection data based on prior information of the at least one hyper parameter 206 then the plurality of observed defect growth rates and the at least one unobserved defect growth rate are simulated based on the simulated hyper parameters 208 and finally defect growth rate point estimate is obtained from the simulated growth rate data 210.

According to an embodiment of the invention the method also involves obtaining a probability of failure of a defect from the defect growth rate point estimates. According to further embodiment of the invention the invention involves updating new defect growth rate data in at least one clusters of defect growth rate so that whenever new defect growths data arises by external inspection/new inspection defect data all defects growths belongs to that cluster would be updated using Hierarchical Bayesian method. It helps the pipeline operators in identifying the major defects and their growth rate and scheduling the inspection of those defects.

According to an exemplary embodiment of the invention if inspection data of few years having different independent defects D1, D2, - - - Dn of n defects as represented in Table 1 where
✓—indicates the observed defect growth
x—indicates the unobserved defect growth

TABLE 1

Inspection data of different defects

| Defects | Inspection Time in Years | | | | | | |
|---|---|---|---|---|---|---|---|
| | 1 | 2 | 3 | 4 | 5 | 6 | 7 |
| D1 | ✓ | x | ✓ | x | x | ✓ | ✓ |
| D2 | ✓ | ✓ | x | ✓ | x | ✓ | x |
| D3 | ✓ | ✓ | ✓ | x | x | ✓ | x |
| . | | | | | | | |
| . | ✓ | x | x | ✓ | x | ✓ | ✓ |
| . | | | | | | | |
| Dn | | | | | | | |

In order to determine unobserved defect growth rate over a period of time based on the observed defect growth rate using Hierarchical Bayesian method assumed that the defects grow independently with respect to time and consider the modeling of defect depth growth using Hierarchical Bayesian method and it is explained below.

Defect depth Growth rate: Let $Y=(Y_1, Y_2, \ldots, Y_n)$ be the defect depth growth rate and assumed that n defects is present each defect grows independently in depth. Each defect has mean growth rate $\theta_{1i}$, and variance $\sigma_{1i}^2$ for $i=1, 2, \ldots, n$ $$(\text{i.e.}) \; \Theta_1 = \begin{pmatrix} \Theta_{11} \\ \Theta_{12} \\ \vdots \\ \Theta_{1n} \end{pmatrix}; \sigma_1^2 = \begin{pmatrix} \sigma_{111}^2 & \cdots & 0 \\ \vdots & \cdots & \vdots \\ 0 & \cdots & \sigma_{1nn}^2 \end{pmatrix}$$

For given $\theta_1$, for illustrative purpose assumed that defect depth growth rate follows multivariate normal distribution such as For a given $\theta_2$, of unknown hyper parameters which is a function of uncertainties such as temperature or stress etc. the parameters $\theta_1$ drawn from the multivariate normal distribution with mean $\theta_2$, and variance $\sigma_2^2$.

$$\Theta_1 \sim N(\Theta_2, \sigma_2^2)$$

$$\text{where } \Theta_2 = \begin{pmatrix} \Theta_{21} \\ \Theta_{22} \\ \vdots \\ \Theta_{2n} \end{pmatrix}; \sigma_2^2 = \begin{pmatrix} \sigma_{211}^2 & \cdots & 0 \\ \vdots & \cdots & \vdots \\ 0 & \cdots & \sigma_{2nn}^2 \end{pmatrix}$$

Here are $\sigma_1^2$, $\sigma_2^2$ known positive definite matrices.

Here $\theta_2$ are the hyper parameters and the prior information about the hyper parameters is known and it has the following distribution U(a, b) where a, b are fixed constants.

Further, in order to estimate the parameters of the depth growth rate even though the growth rates are independent but they are related by the hyper parameters and if the prior information of the hyper parameters are known. (i.e) If any of defect growth rate particular inspection time is known then the unobserved defect growth rate by using observed defect growth rates can be estimated Hence posterior distribution is obtained $P(\theta_1|Y, \theta_2, \sigma_1^2, \sigma_2^2)$ Now considering Bayes theorem, $P(\theta_1|Y)\alpha P(Y|\theta_1)P(\theta_1)$.

From Bayes theorem the posterior distribution of defect growth rate distribution follows N(Bb, B).

Where $B=(\sigma_1^{-2}+\sigma_2^{-2})$ and $b=(\sigma_1^{-2}Y+\sigma_2^{-2}\theta_2)$ The estimates of the each defect growth rate mean is given by $\hat{\theta}_{1i}$ $$\hat{\Theta}_{1i} = \frac{(Y_i/\sigma_{11i}^2 + \Theta_{2i}/\sigma_{21i}^2)}{(\sigma_{11i}^2 + \sigma_{21i}^2)} \text{ for each } i = 1, 2, \ldots, n$$

If the growth rate of any defect at time t ($\theta_{2i}$ for some i) is known then the growth rate of other defects at time t can be computed by using the posterior distribution $\theta_{1i}|\theta_{2i}, Y_i$. Even though the defects depths are independent but they related by its hyper parameters for $\theta_{2i}=\theta_{2j}$ for $i\neq j$; i, j=1, 2, . . . , n Here the close form of the defect growth rate estimates are obtained analytically since the defect growth rates follows the multivariate normal distribution. There are cases when the defect growth rates are not normal and it follows the gamma distributions or Weibull distribution etc. then closed form expression for defect growth estimates is not obtained easily and hence need to simulate the data in two steps.

Step 1: Simulate the hyper parameters from the marginal posterior density of the hyper parameters conditional on the inspection data which is given by $$h(\theta_2|Y)=\Pi_{i=1}^n \int_{\theta_2}^{\infty} \varphi(Y_i/\theta_2)P(\theta_2)d\theta_2$$

where $P(\theta_2)$ is the prior distribution of the hyper parameters.

In the case of normal distribution, $\varphi(Y_i/\theta_2)$ is the probability density function of normal distribution with mean $\theta_2$ and variance $\sigma_2^2$.

Step 2: Simulate the defect growth rates $\theta_1$ conditioning on the simulated hyper parameters and inspection data. The posterior distribution of the defect growth rate parameters is given by $$P(\theta_1|Y)\alpha P(Y|\theta_1)P(\theta_1).$$

In the case of normal distribution the estimates obtained as shown above.

Simulation Approach: According to another exemplary embodiment of the invention Hybrid Monte Carlo (Hamiltonian Monte Carlo) is used to simulate the parameters. The Hamiltonian is constructed as potential term $\varphi(x)=-\log(\pi(x))$ plus a kinetic energy term which is given by $$H = \Phi(x) + \sum \frac{p_i 2}{2m_i}$$

The above example shows the exemplary method for assessing corroded pipeline defect growth rate from partial inspection data.

Figure 3:
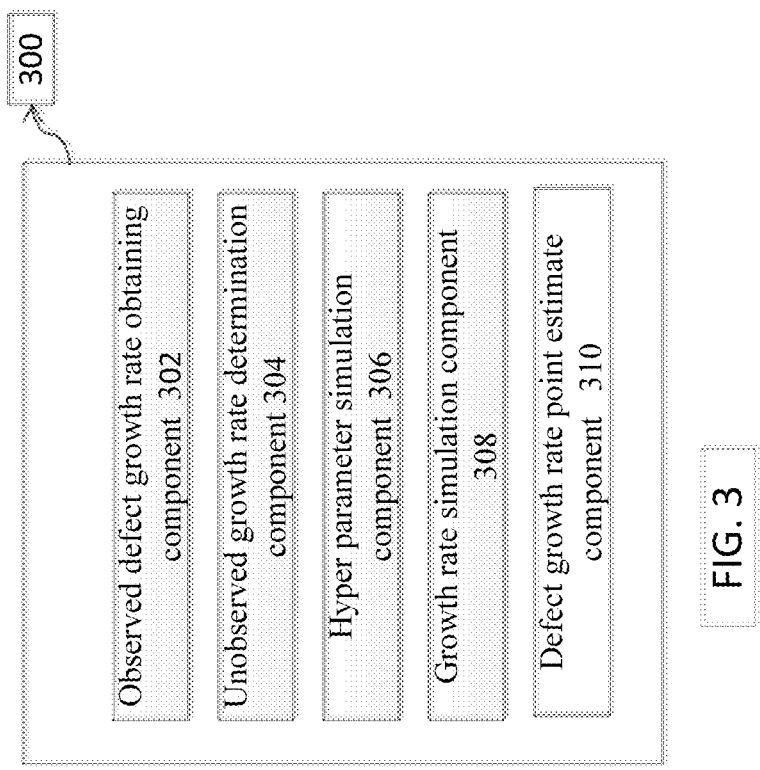
FIG. 3 is a block diagram illustrating a system for illustrating a system for assessing corroded pipeline defect growth rate from partial inspection data, in accordance with an embodiment of the present technique.

FIG. 3 is a block diagram illustrating a system for assessing corroded pipeline defect growth rate from partial inspection data, in accordance with an embodiment of the present technique. More particularly system includes an observed defect growth rate obtaining component 302, an unobserved growth rate determination component 304, a hyper parameter simulation component 306, a growth rate simulation component 308 and a defect growth rate point estimate component 310. The observed defect growth rate obtaining component is configured to obtain a plurality of observed defect growth rates from the inspection data collected at different time intervals. The unobserved growth rate determination component is configured to determine at least one unobserved defect growth rate on the basis of distribution pattern of the plurality of observed defect growth rates. The hyper parameter simulation component configured to simulate, condition of at least one hyper parameter on the inspection data based on prior information of the at least one hyper parameter. The growth rate simulation component configured to simulate the plurality of observed defect growth rates and the at least one unobserved defect growth rate based on the simulated hyper parameters. The defect growth rate point estimate component configured to obtain defect growth rate point estimate from the simulated growth rate data.

The above mentioned description is presented to enable a person of ordinary skill in the art to make and use the invention and is provided in the context of the requirement for obtaining a patent. Various modifications to the preferred embodiment will be readily apparent to those skilled in the art and the generic principles of the present invention may be applied to other embodiments, and some features of the present invention may be used without the corresponding use of other features. Accordingly, the present invention is not intended to be limited to the embodiment shown but is to be accorded the widest scope consistent with the principles and features described herein.

What is claimed is:

1. A method for assessing a corroded pipeline defect, the method comprising:
    obtaining, by a pipeline analysis computing device, a plurality of observed defect growth rates from inspection data collected at different time intervals, wherein the inspection data comprises partial defect growth rate information;
    determining, by the pipeline analysis computing device, at least one unobserved defect growth rate on the basis of distribution pattern of the plurality of observed defect growth rates;
    simulating, by the pipeline analysis computing device, a condition of at least one hyper parameter on the inspection data based on prior information of the at least one hyper parameter;
    simulating, by the pipeline analysis computing device, the plurality of observed defect growth rates and the at least one unobserved defect growth rate based on the simulated hyper parameters;
    obtaining, by the pipeline analysis computing device, a defect growth rate point estimate from the simulated growth rate data; and
    obtaining, by the pipeline analysis computing device, a probability of failure of a defect from the defect growth rate point estimates; and
    scheduling, by the pipeline analysis computing device, an inspection of the defect based on the obtained probability of failure.

2. The method as claimed in claim 1 further comprising updating, by the pipeline analysis computing device, a new defect growth rate data in at least one cluster of defect growth rate.

3. The method as claimed in claim 1, wherein the hyper parameters, the plurality of observed defect growth rates, and the at least one unobserved defect growth rate are simulated by one or more Markov Chain Monte Carlo Methods.

4. The method as claimed in claim 1, wherein the unobserved defect growth rate is determined by a Hierarchical Bayesian method.

5. A pipeline analysis computing device comprising a processor and a memory coupled to the processor which is configured to be capable of executing programmed instructions comprising and stored in the memory to:
   obtain a plurality of observed defect growth rates from inspection data collected at different time intervals, wherein the inspection data comprises partial defect growth rate information;
   determine at least one unobserved defect growth rate on the basis of a distribution pattern of the plurality of observed defect growth rates;
   simulate a condition of at least one hyper parameter on the inspection data based on prior information of the at least one hyper parameter;
   simulate the plurality of observed defect growth rates and the at least one unobserved defect growth rate based on the simulated hyper parameters; and
   obtain a defect growth rate point estimate from the simulated growth rate data;
   obtain a probability of failure of a defect from the defect growth rate point estimates; and
   schedule an inspection of the defect based on the obtained probability of failure.

6. The device as claimed in claim 5, wherein the processor coupled to the memory is further configured to be capable of executing at least one additional programmed instruction comprising and stored in the memory to update a new defect growth rate data in at least one cluster of defect growth rate.

7. The device as claimed in claim 5, wherein the hyper parameters, the plurality of observed defect growth rates, and the at least one unobserved defect growth rate are simulated by one or more Markov Chain Monte Carlo Methods.

8. The device as claimed in claim 1, wherein the unobserved defect growth rate is determined by a Hierarchical Bayesian method.

9. A non-transitory computer readable medium having stored thereon instructions for assessing corroded pipeline defect growth rate comprising machine executable code which when executed by at least one processor, causes the at least one processor to perform steps comprising:
   obtaining a plurality of observed defect growth rates from the inspection data collected at different time intervals, wherein the inspection data comprises partial defect growth rate information;
   determining at least one unobserved defect growth rate on the basis of distribution pattern of the plurality of observed defect growth rates;
   simulating a condition of at least one hyper parameter on the inspection data based on prior information of the at least one hyper parameter;
   simulating the plurality of observed defect growth rates and the at least one unobserved defect growth rate based on the simulated hyper parameters; and
   obtaining a defect growth rate point estimate from the simulated growth rate data;
   obtaining a probability of failure of a defect from the defect growth rate point estimates; and
   scheduling an inspection of the defect based on the obtained probability of failure.

10. The non-transitory computer readable medium as claimed in claim 9 further having stored thereon at least one additional instruction that when executed by the processor cause the processor to perform at least one additional step comprising updating a new defect growth rate data in at least one cluster of defect growth rate.

11. The non-transitory computer readable medium as claimed in claim 9, wherein the hyper parameters, the plurality of observed defect growth rates, and the at least one unobserved defect growth rate are simulated by one or more Markov Chain Monte Carlo Methods.

12. The non-transitory computer readable medium as claimed in claim 9, wherein the unobserved defect growth rate is determined by a Hierarchical Bayesian method.

* * * * *